United States Patent [19]

Nakamura et al.

[11] Patent Number: 4,636,643

[45] Date of Patent: Jan. 13, 1987

[54] FOG DETECTING APPARATUS FOR USE IN VEHICLE

[75] Inventors: Kanehito Nakamura, Oobu; Kazuma Matsui, Toyohashi; Takashi Kurahashi, Aichi; Hiroshi Ishikawa, Nagoya, all of Japan

[73] Assignee: Nippondenso Co., Ltd., Kariya, Japan

[21] Appl. No.: 634,360

[22] Filed: Jul. 25, 1984

[30] Foreign Application Priority Data

| Jul. 25, 1983 | [JP] | Japan | 58-136374 |
| Jul. 25, 1983 | [JP] | Japan | 58-136375 |
| Jul. 25, 1983 | [JP] | Japan | 58-136376 |
| Jul. 25, 1983 | [JP] | Japan | 58-138617 |

[51] Int. Cl.$^4$ .................. G01N 21/55; B60L 1/02
[52] U.S. Cl. ........................... 250/338; 250/341; 250/349; 219/203; 356/448
[58] Field of Search ............ 250/341, 338, 339, 349; 356/445, 448; 219/203; 318/483

[56] References Cited

U.S. PATENT DOCUMENTS

| 3,555,289 | 1/1971 | Sobkow | 318/483 |
| 4,132,881 | 1/1979 | Ciarniello et al. | 219/203 |
| 4,266,878 | 5/1981 | Auer | 250/339 |
| 4,355,271 | 10/1982 | Noack | 318/483 |

FOREIGN PATENT DOCUMENTS

| 56-87846 | 7/1981 | Japan | 356/445 |
| 161849 | 9/1983 | Japan | 356/445 |
| 699405 | 11/1979 | U.S.S.R. | 356/448 |

Primary Examiner—Carolyn E. Fields
Attorney, Agent, or Firm—Cushman, Darby & Cushman

[57] ABSTRACT

In a fog detecting apparatus with optoelectronic system, comprising infrared-emitting means and infrared-receiving means, is provided means for adjusting a reference which is compared with a voltage value of a detecting signal generated according to an electrical signal produced by the infrared-receiving means in order to distinguish whether a windshield of a vehicle is in the fogging condition or not. The reference is changed according to the detecting signal which is produced when the windshield is in good condition against the fogging after a fog removing apparatus has been actuated to remove the fog attached on the windshield, so that the fogging condition is detected in accuracy independently of the contamination of the optoelectronic system or the like.

5 Claims, 14 Drawing Figures

FOG DETECTING APPARATUS FOR USE IN VEHICLE

BACKGROUND OF THE INVENTION

This invention relates to a fog detecting apparatus, and more particularly to a fog detecting apparatus for use in a vehicle, using optoelectronic system.

It is known that various types of fog detecting apparatus, which detect the fogging condition on a windshield of a vehicle, are employed and a fog removing apparatus such as a defroster is provided in the vehicle for preventing a traffic accident caused by the poor visibility.

In one type of such apparatus, an optoelectronic system is used, such as is disclosed in Japanese Utility Model Publication No. 55-3408, comprising light-emitting means actuated in response to a signal from an emitting control circuit, and light-receiving means for receiving the light emitted from the light-emitting means and for producing an electrical signal being in proportion to the intensity of the received light. The fogging condition on the windshield is detected on the basis of the electrical signal.

On the other hand, it is intended that the fog removing apparatus is automatically controlled according to the electrical signal so as to adequately remove the fog from the windshield.

However, it is actually difficult to produce the electrical signal corresponding to the fogging condition accurately due to a secular change and the contamination of the optoelectronic system or the like, and thereby adequate control of the fog removing apparatus is not ensured.

Furthermore, because of the disproportion of the fogging condition on the windshield, although the fog removing apparatus has been actuated according to the electrical signal, the fog existing on portions of the windshield required for a safe drive is not completely removed and some of the fog may remain. Namely, when the fogging is detected at the detecting portion of the windshield, the fog removing apparatus is arranged to be actuated, and when the fogging thereat is removed, the fog removing apparatus is arranged to be stopped no matter whether all fog is actually removed or not.

Still furthermore, in the case that the fog is not completely removed, a period fogged again becomes shorter and the cycle of actuation and stopping of the fog removing apparatus becomes shorter, resulting in an uncomfortable driving of the vehicle.

SUMMARY OF THE INVENTION

It is, therefore, an object of the present invention to provide a fog detecting apparatus which is capable of adequately controlling a fog removing apparatus.

A further object of the present invention is to detect the fog on a windshield of a vehicle in accuracy irrespective of the disproportion of the fogging condition.

A still further object of the present invention is to ensure an actuation of a fog removing apparatus until the fog on a windshield is completely removed.

According to a feature of the present invention, in a fog detecting apparatus using an optoelectronic system there is provided means for adjusting a reference which is compared with a detecting signal produced on the basis of an electrical signal generated by a light-receiving means in order to distinguish whether a windshield is fogged or not. The reference is changed according to the detecting signal produced when the windshield is in good condition against the fogging after a fog removing apparatus has been actuated to remove the fog attached on a windshield, so that the fog is detected accurately independently of the contamination of the optoelectronic system or the like.

According to another feature of the present invention, a plurality of optoelectronic systems, comprising a light-emitting means and a light-receiving means, are provided so as to detect each fogging condition on a plurality of detecting portions of a windshield, so that the fog is accurately detected independently of the disproportion of the fogging condition.

According to a further feature of the present invention, in a fog detecting apparatus there is provided a timer circuit for successively applying a signal for actuating a fog removing apparatus in a predetermined period without regard to the improvement from the fogging condition caused by the fog removing apparatus in order to remove the fog completely. The signal for actuating the fog removing apparatus is produced by a comparison circuit for comparing a detecting signal produced by a detector with a threshold. According to a further feature of the present invention, in a fog detecting apparatus there is provided first and second light-receiving means for receiving the light emitted from a light-emitting means. The second light-receiving means is used for establishing a reference to be compared with signals produced by the first light-receiving means for determining whether a windshield is fogged or not. The second light-receiving means is arranged to directly receive the light from a light-emitting means, so that the reference corresponds to the condition in which the fog is completely removed and the fog is detected accurately by comparing a signal produced by the first light-receiving means with a signal produced by the second light-receiving means, without regard to the contamination of the light-emitting means or the like.

Other and further objects and features of this invention will become obvious upon an understanding of the illustrative embodiments about to be described or will be indicated in the appended claims, and various advantages not referred to herein will occur to one skilled in the art upon employment of the invention in practice.

BRIEF DESCRIPTION OF THE DRAWINGS

The present invention will be described in further detail with reference to the accompanying drawings in which.

DETAILED DESCRIPTION OF THE PREFERRED EMBODIMENT

Figure 1:
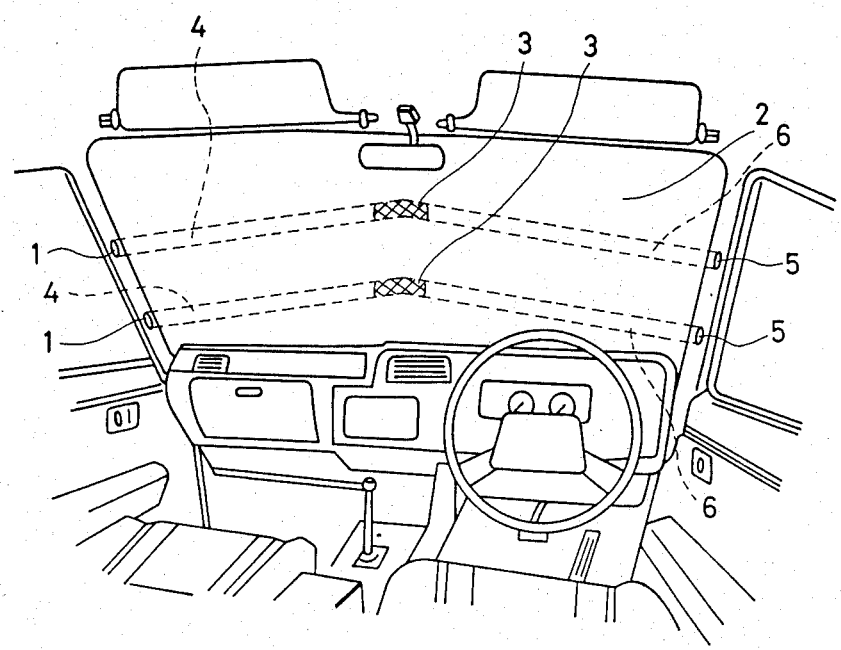
FIG. 1 is a perspective side view of the inside of a vehicle employing a fog detecting apparatus according to the present invention.

Referring now to the drawings, FIG. 1 shows the inside of a vehicle employing a fog detecting apparatus with an optoelectronic system according to the present invention. The optoelectronic system comprises infrared-emitting means 1 and infrared-receiving means 5. The infrared-emitting means comprises a light-emitting element such as a light-emitting diode and a condensing lens, and is arranged such that an infrared beam 4 emitted therefrom is directed to each of detecting portions 3 provided on a windshield 2. The infrared-receiving means 5 comprises a light-receiving element such as a photodiode and a condensing lens, and is arranged to receive an infrared beam 6 reflected on the detecting portions 3 of the windshield 2. The infrared-emitting means 1 and the infrared-receiving means 5 are respectively disposed on a frame of the windshield 2 as opposed to each other. In the figure, two combinations of the infrared-emitting means 1 and the infrared-receiving means are shown thereon.

In this arrangement, the infrared-emitting means 1 emits an infrared beam to each of the detecting portions 3 in response to a signal from an emitting control circuit (not shown). The infrared beams incident on the detecting portions 3 are reflected thereon and are received by the infrared-receiving means 5. The infrared-receiving means produces an electrical signal corresponding to the intensity of the received infrared beam. A fogging condition on the windshield is detected on the basis of the electrical signal. Namely, some of the infrared beam incident on the detecting portions 3 is scattered thereon in proportion to the fogging condition thereof, and thereby the intensity of the beam incident on the infrared-receiving means 5 is decreased.

Figure 2:
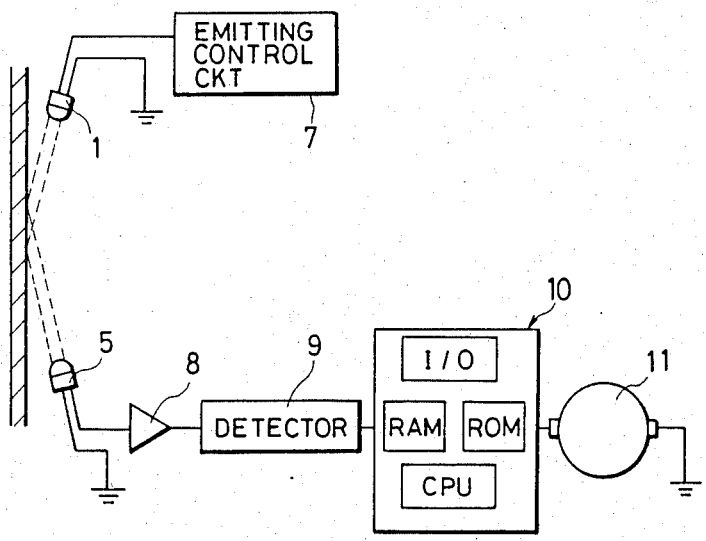
FIG. 2 is a schematic block diagram of a fog detecting apparatus according to a first embodiment of the present invention.

FIG. 2 is a schematic block diagram of a fog detecting apparatus according to a first embodiment of the present invention. Designated at the reference 1 is an infrared-emitting means for emitting an infrared beam in response to a signal from an emitting control circuit 7. The infrared beam emitted from the infrared-emitting means 1 is received by an infrared-receiving means 5 which generates an electrical signal corresponding to the intensity of the received beam. The electrical signal is fed to a detector 9 through an amplifier 8, for generating a detecting signal. The detecting signal is fed to a control uniti 10 such as a well known microcomputer having a central processing unit (CPU), memories, input/output device (I/O) and the like. The control unit 10 is associated with a fog removing apparatus 11, such as a defroster, a device for heating wires provided in a windshield or the like, which removes the fog existing on a windshield of a vehicle. The control unit 10 operates the fog removing apparatus according to a voltage value from the detector 9. A number of the amplifier 8, the detector 9 and the control unit 10 corresponds to a number of the infrared-emitting means 1 and the infrared-receiving means 5, and they are arranged to actuate the fog removing apparatus 11 when, at least, the fog is detected at one of detecting portions established on the windshield. For the purpose of it, OR circuit will be adapted.

Figure 3:
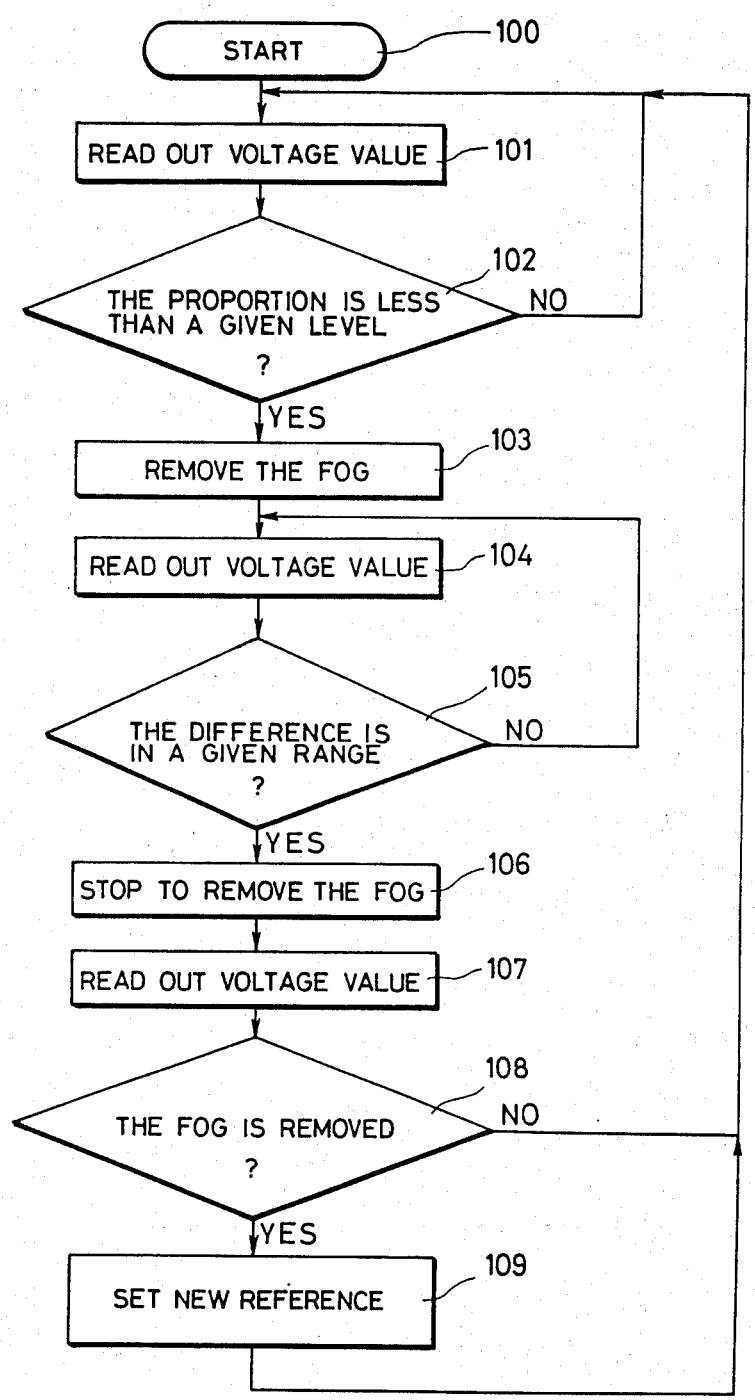
FIG. 3 is a flow diagram associated with the microcomputer of FIG. 2.

FIG. 3 is a flow diagram showing an operation performed in the control unit 10. At the beginning of the operation, initialization (start 100) is effected when a key for starting an engine of a vehicle is turned ON, and then the following step 101 is executed. In the step 101, a voltage value of an analog signal from the detector 9 is converted to a digital signal, and a data corresponding to the digital signal is prestored in a memory.

In a following step 102 is operated the proportion of a voltage value corresponding to the prestored data to a given voltage value, that is a reference. If the proportion is less than a predetermined level, for example, less than 75%, it is estimated that a windshield of a vehicle will be in the fogging condition, and a following step 103 is executed. On the other hand, if more than the predetermined level, the step 101 and 102 are repeatedly executed.

In the step 103, the control unit 10 feeds a signal for actuating the fog removing apparatus thereto, and then the fog removing apparatus is actuated and thereby a voltage value from the detector 9 becomes higher gradually. In a step 104, the voltage value is read out as well as the step 101.

In a following step 105, the difference between the voltage values read out successively is operated, and the control unit 10 gives a decision whether the difference is in a given range or not. The step 104 and 105 are repeatedly executed. If the difference is in the given range and is stable, a following step 106 is executed. Namely, in this case, it has the meaning that the fog on the windshield has been removed and the reflecting rate on the detecting portions 3 is stable. Even if air in a compartment of a vehicle is polluted by smoke, the reflecting rate is also stable. In the step 106, the control unit 10 stops the operation of the fog removing apparatus 11. And a following step 107 is executed.

In the step 107, a voltage value from the detector 9 is read out. Since the voltage value read out in the step 107 has an effect with respect to a change with the passage of time and the contamination of the optoelectronic system or the like, the voltage value will be used as a reference in a following step 109 for detecting the fogging condition in accurately.

In a following step 108, the control unit 10 checks again whether the fog is completely removed or not. The proportion of the voltage value read out in the step 107 to the given voltage value is operated and is compared with a given level, for example 95%. If the proportion is more than the given level, a following step 109 is executed. If the proportion is less than the given level, the operation returns to the step 101. Namely, the given level is a standard for determining whether the reference is changed in a following step 109 or not. The given level is determined in considering a change with the passage of time of the optoelectronic system and the like.

In the step 109, the voltage value in the step 107 is stored in a memory as a new reference. Even if a key for starting an engine of a vehicle has been turned OFF, the new reference is continuously stored in the memory, and is used as a reference in the step 102 when the key for starting an engine of a vehicle is turned ON again.

In the step 102 and 108, it is possible to change the operation such that the fogging condition is detected by the difference between the voltage value and the reference.

Figure 4A:
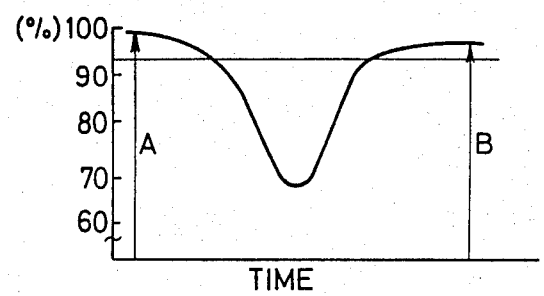
FIG. 4A and 4B are charts showing the proportion of a voltage value of a signal from a detector with a reference.
Figure 4B:
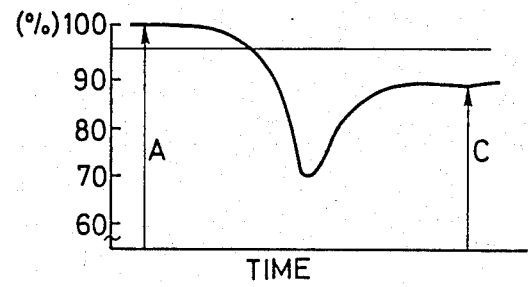

FIG. 4A and 4B are charts showing the changing of a proportion of a voltage value from the detector 9 to a reference. A reference A designates a proportion in the condition which the fog is not occured, and references B and C designate a proportion in the condition which the fog is removed by the fog removing apparatus 11 after it is occured.

In FIG. 4A, since the proportion in reference B is more than a given level (95%), the reference (voltage value) will be changed in the step 109. In FIG. 4B, since the proportion in reference C is less than the given level (95%), the reference will not be changed and the operation returns to the step 101.

Figure 5:
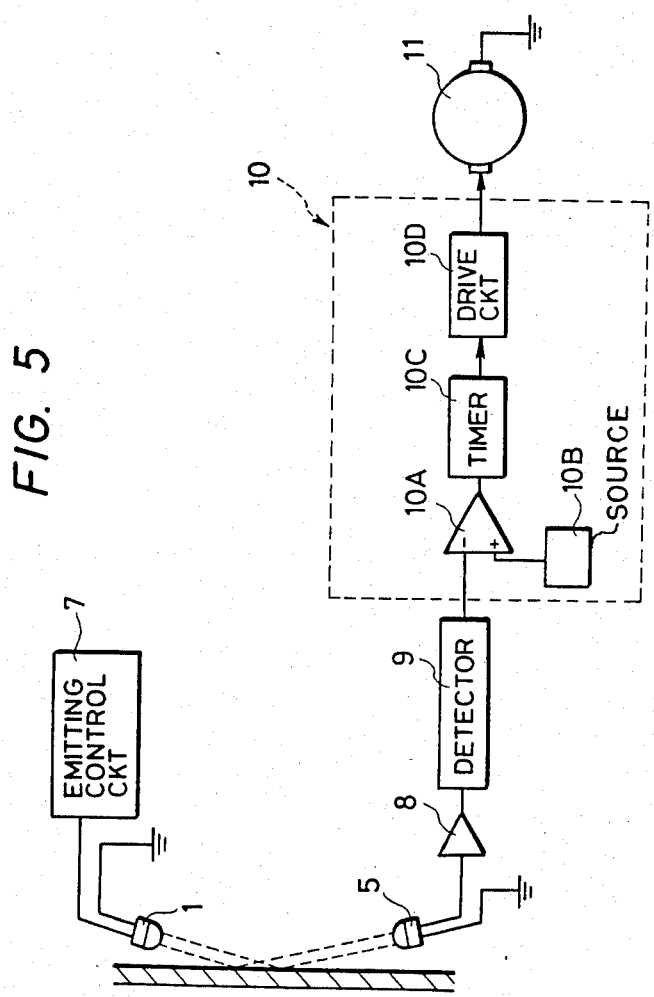
FIG. 5 is a schematic block diagram of a fog detecting apparatus according to a second embodiment of the present invention.

FIG. 5 is a schematic block diagram of a fog detecting apparatus according to a second embodiment of the present invention. As well as the fog detecting apparatus described in FIG. 2, the fog detecting apparatus according to a second embodiment comprises an infrared-emitting means 1 for emitting an infrared beam in response to a signal from an emitting control circuit 7, an infrared-receiving means 5 for generating an electrical signal corresponding to the intensity of the infrared beam received, an amplifier 8 for amplifying an output signal of the infrared-receiving means 5, a detector 9 for generating a detecting signal and a control unit 10 for controlling a fog removing apparatus 11. The control unit 10 according to a second embodiment comprises a comparator circuit 10A for comparing an output signal of the detector 9 with a threshold predetermined by a source 10B, a timer circuit 10C for switching off a signal for actuating the fog removing apparatus after a predetermined delay and a driving circuit 10D for actuating the fog removing apparatus 11.

The comparator circuit 10A has hysteresis, so that it feeds a signal to the timer circuit 10C when a voltage value of the detecting signal from the detector 9 has become lower than a threshold and it stops to feed a signal to the timer circuit 10C when a voltage value of the detecting signal therefrom has become higher than a threshold. The hysteresis is obtained by means of a positive feedback with a resistor which is well known. A number of the comparator circuit 10A corresponds to a number of the infrared-emitting means 1 and the infrared-receiving means 5. If a plurality of the infrared-emitting means 1 and the infrared-receiving means 5 is employed, OR circuit will be provided between the comparator circuit 10A and the timer circuit 10C so as to cause the fog removing apparatus 11 to actuate in response to, at least, one of output signals of the comparator circuits 10A.

In this arrangement, when a voltage value of a signal from the detector 9 becomes lower than a threshold, the comparator circuit 10A generates a signal for actuating the fog removing apparatus 11. While the comparator circuit 10A stops to generate the signal when a voltage value of a signal from the detector 9 becomes higher than a threshold by actuating the fog removing apparatus 11. However, the timer circuit 10C functions such that the fog removing apparatus is successively actuated for a predetermined period. Therefore, the fog is completely removed without regard to the disproportion of the fogging condition. Even if fog remains on portions other than detecting portions, the remained fog is removed meanwhile. The hysteresis of the comparator circuit 10A together with the timer circuit 10C results in the prevention of occurrence of hunting and completely removes fog. The period for delay can be adjusted according to the hysteresis. When the hysteresis is great, the period can be made short.

In the second embodiment described above, it is possible to perform the function of the control unit 10 by using a microcomputer.

Figure 6:
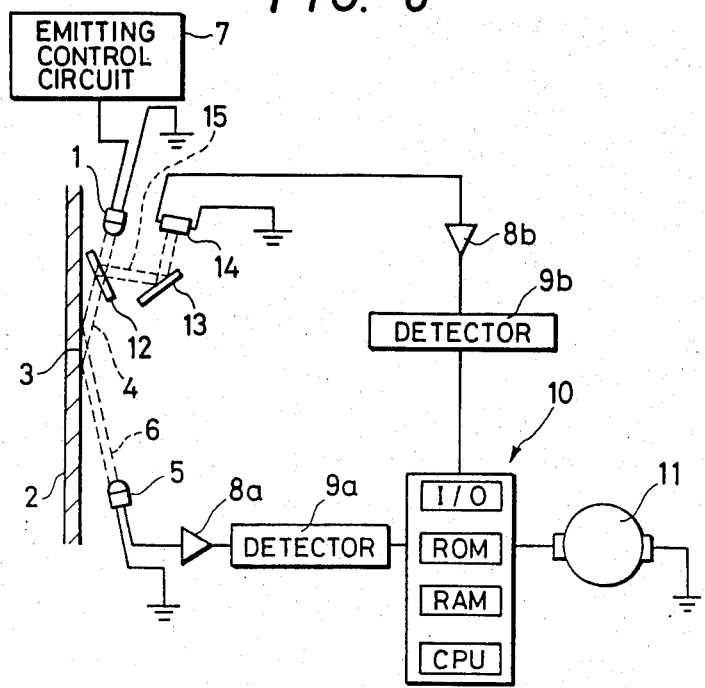
FIG. 6 is a schematic block diagram of a fog detecting apparatus according to a third embodiment of the present invention.

FIG. 6 is a schematic block diagram showing a fog detecting apparatus according to a third embodiment of the present invention. Designated at a reference 1 is an infrared-emitting means for emitting an infrared beam in response to a signal from an emitting control circuit 7. The infrared beam emitted from the infrared-emitting means 1 is divided into two beams 4 and 15 by a light-dividing means 12 such as half-mirror. One beam 4 is received by a first infrared-receiving means 5 which generates an electrical signal corresponding to the intensity of the received beam 6, after being reflected on a detecting portion 3 of a windshield 2. The electrical signal is fed to a detector 9a through an amplifier 8a, for generating a detecting signal. The detecting signal is fed to a control unit 10 such as a well known microcomputer having a central processing unit (CPU), memories, input/output device and the like. The other beam 15 is received by a second infrared-receiving means 14 after being reflected by a mirror 13. An electrical signal generated by the second infrared-receiving means 14 is fed to a detector 9b through an amplifier 8b, for generating a detecting signal which is fed to the control unit 10. The control unit 10 is associated with a fog removing apparatus 11, such as a defroster, a device for heating wires provided in a windshield or the like, which removes the fog existing on a windshield of a vehicle.

Figure 7:
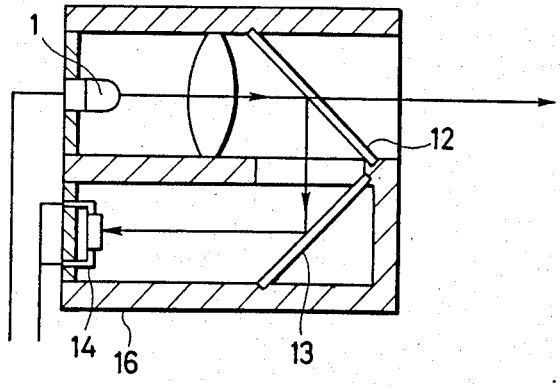
FIG. 7 is a cross-sectional view of the infrared-emitting means and the second infrared-receiving means in FIG. 6.

FIG. 7 is a cross-sectional view showing an arrangement in connection with the infrared-emitting means 1, the second infrared-receiving means 14, the light-dividing means 12 and the mirror 13. They are arranged in a casing 16 for making compact. In this case, it is desired that the casing 16 is sealed after humid air is removed or is made of a material with low thermal conductivity, for avoiding the influence from the outside air temperature.

Figure 8:
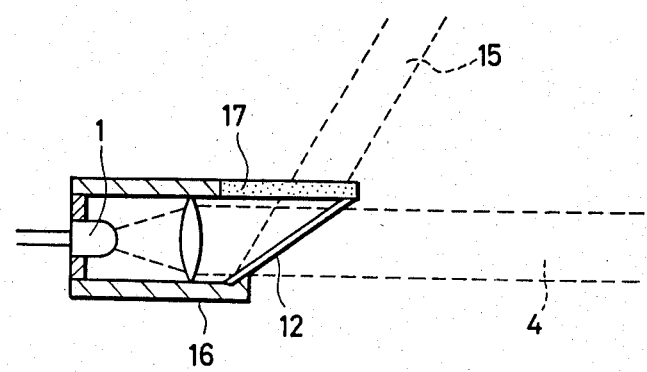
FIG. 8 is a cross-sectional view of the infrared-emitting means in FIG. 6.
Figure 9:
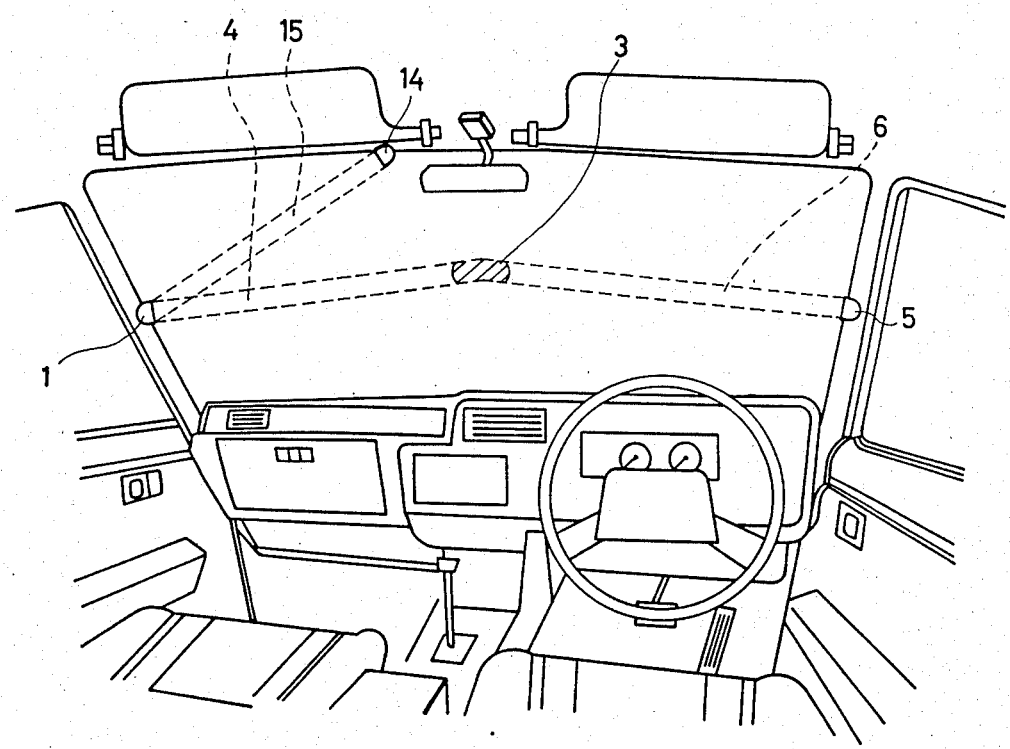
FIG. 9 is a perspective side view of the inside of a vehicle employing a fog detecting apparatus according to a third embodiment of the present invention.

FIG. 8 is a cross-sectional view showing the other arrangement, and FIG. 9 is a view showing a disposition in a vehicle.

An infrared beam is divided into two beams by a light-dividing means 12. One beam is directed to a detecting portion 3, and a beam 6 reflected thereon is received by a first infrared-receiving means 5. On the other hand, the other beam is directed to a second infrared-receiving means 14 through a transparent portion 17 of a casing 16.

The signal generated by the second infrared-receiving means 14 and fed to the control unit 10 through the amplifier 8b and the detector 9b indicates an actual intensity of a beam emitted from the infrared-emitting means 1 at a point of time. Generally, the intensity of the emitted beam is changed according to a change with the passage of time and the contamination of the optoelectronic system. If the fogging condition on a windshield is detected by comparing a detecting signal with a predetermined reference, the fogging condition cannot be detected accurately. Therefore, the signal generated by the second infrared-receiving means 14 is employed as a reference, so that the actual fogging condition can be always detected accurately without regard to the changing caused by a secular change and the contamination of the optoelectronic system or the like. Particularly, the actual fogging condition is accurately detected from a time of turning on a key for starting an engine of a vehicle because an adequate reference is established by the signal generated by the second infrared-receiving means 14 on the turning.

Figure 10:
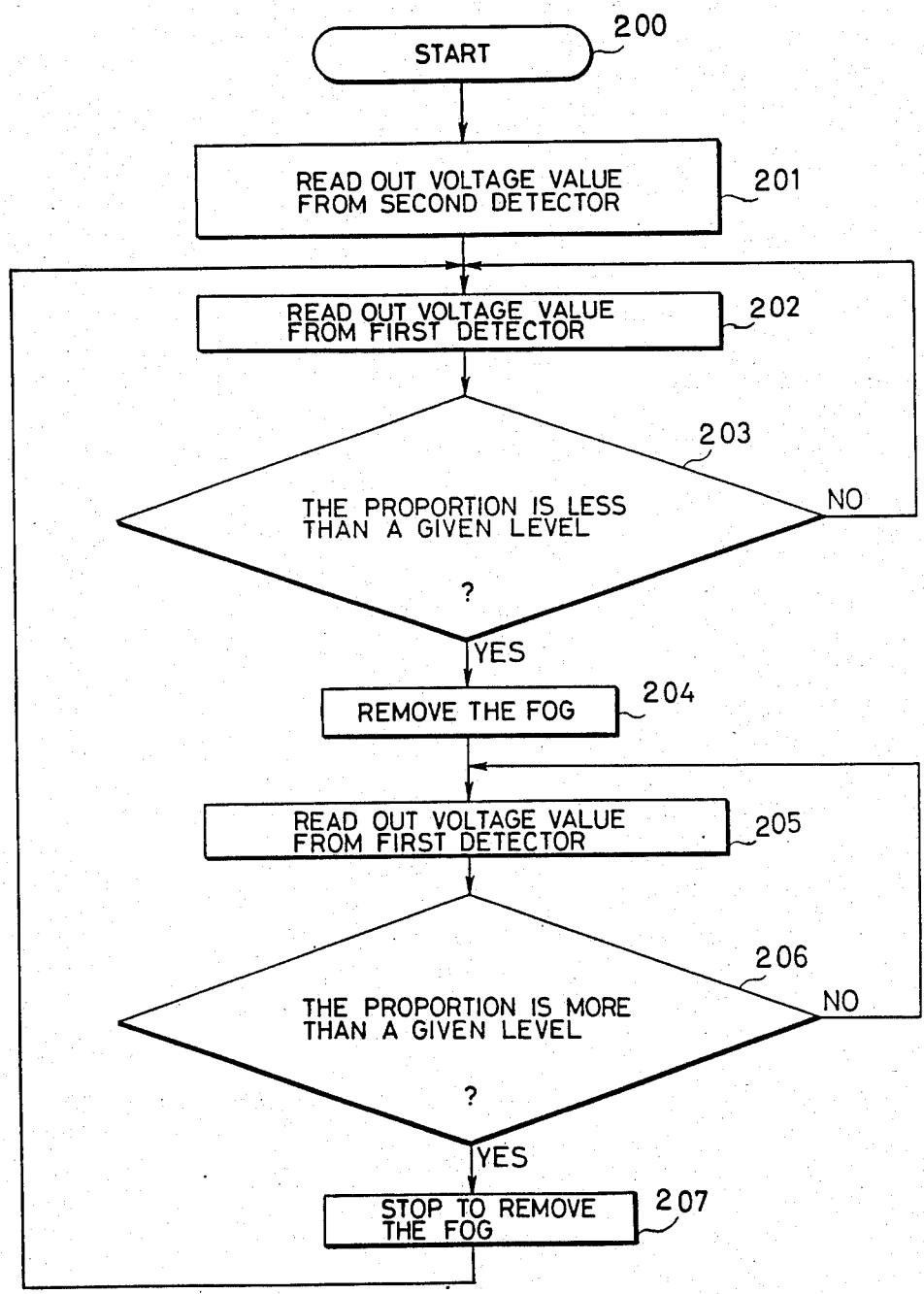
FIG. 10 is a flow diagram associated with the microcomputer in FIG. 6.

FIG. 10 is a flow diagram showing an operation performed in the control unit 10. At the beginning of the operation, initialization (step 200) is effected when a key for starting an engine of a vehicle is turned on, and then a following step 201 is executed. In the step 101, a voltage value of an analog signal fed by the detector 9b is converted to a digital signal, and data corresponding to the digital signal is prestored in a memory. The data is used as a reference.

In a following step 202, a voltage value of an analog signal fed by the detector 9a is converted to a digital signal, and a data corresponding to the digital signal is prestored in a memory.

Nextly, in a following step 203 is operated a proportion of the voltage value prestored in the step 201 to the voltage value prestored in the step 202. If the proportion is more than a predetermined level, it is estimated that a windshield of a vehicle will be in the fogging condition, and a following step 204 is executed. On the other hand, if less than the predetermined level, the step 202 and 203 will be repeatedly executed.

In the step 204, the control unit 10 feeds a signal for actuating the fog removing apparatus 11 thereto, and then the fog removing apparatus is actuated and thereby a voltage value from the detector 9a becomes higher gradually. In a step 205, the voltage value is read out as well as in the step 202.

In a following step 206, the proportion is operated as well as in the step 203 and is compared with the predetermined level. If the proportion is more than the predetermined level, a following step 207 is executed. If less than the predetermined level, the steps 205 and 206 are repeatedly executed. In the step 207, the control unit 10 stops the operation of the fog removing apparatus 11.

Returning to FIG. 1, two combinations of the infrared-emitting means 1 and the infrared-receiving means 5 are employed for detecting the fogging condition on two detecting portions of a windshield 2 of a vehicle. Generally, the fogging condition is apt to have the lack of uniformity due to a temperature distribution of a windshield. For a safety drive, it is necessary that all fog on the windshield is removed. Therefore, it is desired to detect the fogging condition on a plurality of portions of a windshield by a plurality of infrared-emitting means and infrared-receiving means.

Figure 11:
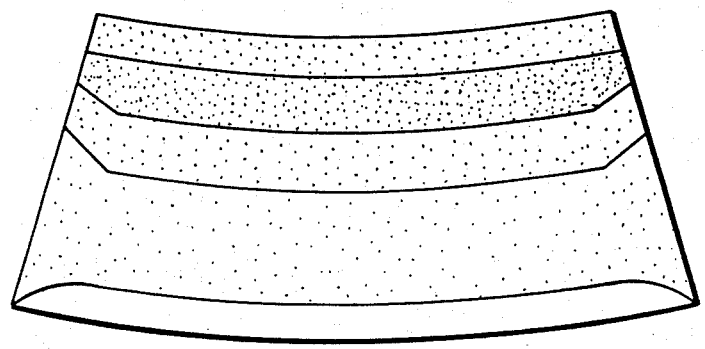
FIG. 11 is a view showing the fogging condition of a windshield.

On the other hand, the lack of uniformity is apt to occur in longitudinal direction as a defroster is generally arranged so as to send the heated air to upper portion of the windshield from lower portion. FIG. 11 shows the lack of uniformity. In the figure, a number of spot indicates a degree of the fogging condition. In view of this point, it is desired that the detecting portions are established in longitudinal direction.

Figure 12:
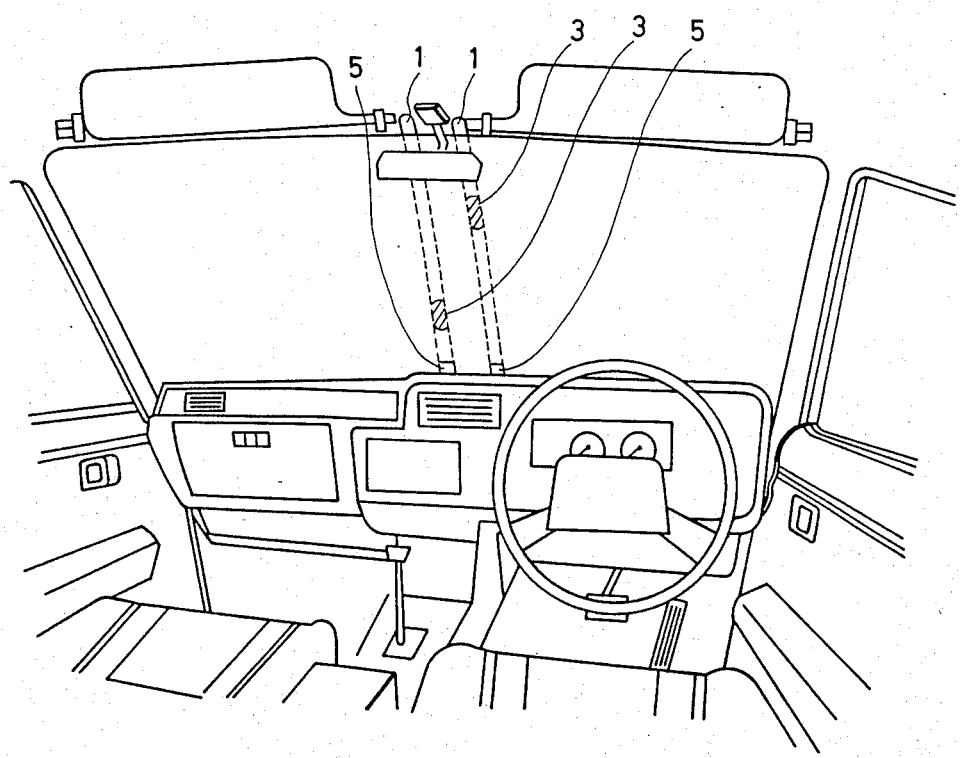
FIG. 12 is a perspective side view of the inside of a vehicle employing a fog detecting apparatus according to the present invention.

FIG. 12 shows another disposition of an optoelectronic system. Infrared-emitting means 1 and infrared-receiving means 5 are disposed in longitudinal direction, and detecting portions 3 are established in longitudinal direction.

Figure 13:
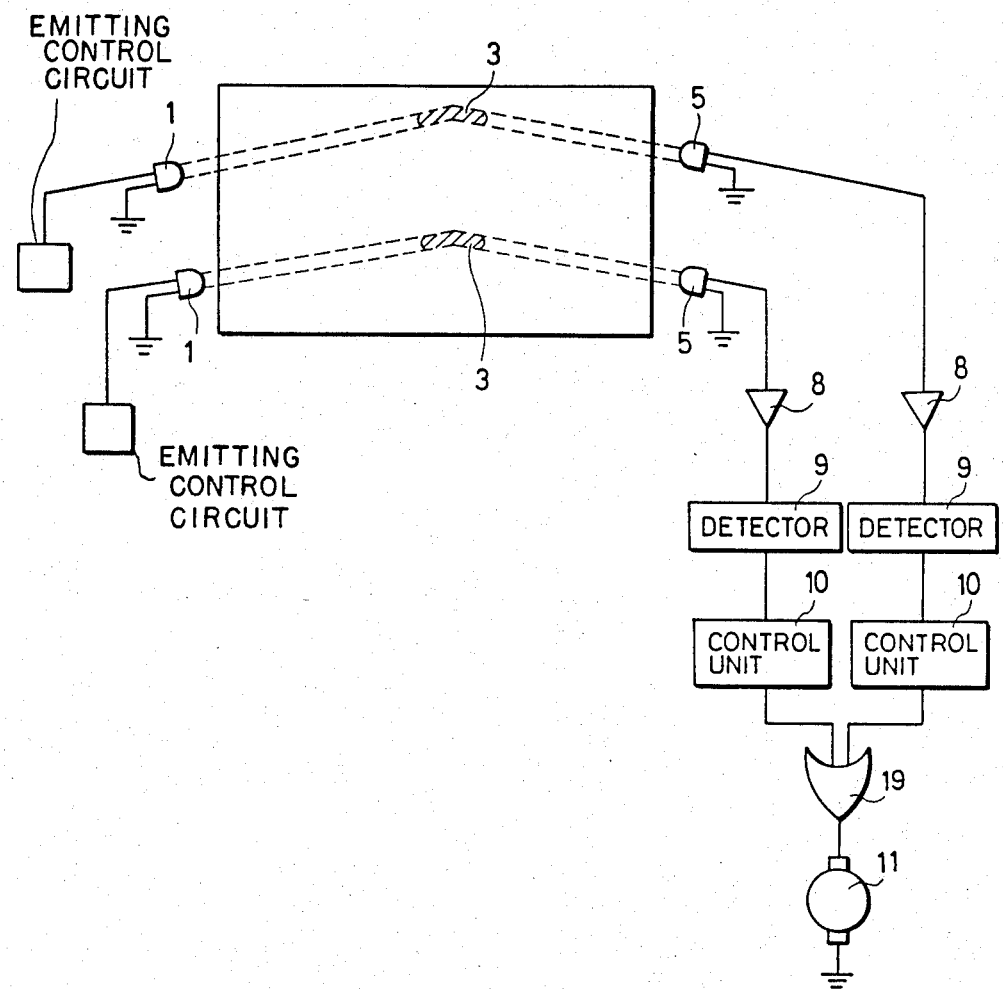
FIG. 13 is a schematic block diagram of a fog detecting apparatus according to the present invention.

FIG. 13 is a schematic block diagram showing a fog detecting apparatus according to the present invention. As described above, a plurality of infrared-emitting means 1 and infrared-receiving means 5 is employed for detecting the fogging condition accurately against the disproportion. In this case, signals generated by each of the infrared-receiving means 5 are respectively fed to each of control units 10 through amplifiers 8 and detectors 9, and each of output signals of the control units 10 is fed to an OR circuit 19. A fog removing apparatus 11 is arranged to be actuated according to an output signal of the OR circuit 19. Therefore, when, at least, the fog is detected at one of detecting portions established on a windshield.

What is claimed is:

1. A fog detecting apparatus for use in a vehicle, comprising:
   (a) means for emitting an infrared beam such that the emitted infrared beam is directed to a predetermined portion of a wndshield of said vehicle, said infrared-emitting means being actuated in response to a signal applied thereto from an emitting control circuit;
   (b) means for receiving an infrared beam reflected at said predetermined portion, said infrared-receiving means producing an electrical signal corresponding to an intensity of an infrared beam reaching said infrared-receiving means after a reflection;
   (c) means for detecting a fog on said windshield by comparing said electrical signal from said infrared-receiving means with a predetermined reference value and issuing a command signal indicative of the removal of the fog in response to the detection of the fog;
   (d) first decision means for deciding that the fluctuation of said electrical signal is stably kept within a first predetermined range, after the removal of the fog performed in response to said command signal;
   (e) second decision means for deciding that the deviation between said electrical signal and said predetermined reference value remains within a second predetermined range, after the decision of stability of the fluctuation; and
   (f) means for updating said predetermined reference value with a value of said electrical signal at the time that a decision is made by said second decision means.

2. A fog detecting apparatus as claimed in claim 1, further comprising means for causing the updating of said predetermined reference value to be prohibited when the deviation is beyond said second predetermined range.

3. A fog detecting apparatus as claimed in claim 1, further comprising means for causing the updated reference value to be retained irrespective of the turn-off of a key switch of said vehicle.

4. A fog detecting apparatus for use in a vehicle, comprising:
   (a) means for emitting an infrared beam such that the emitted infrared beam is directed to a predetermined portion of a windshield of said vehicle, said infrared-emitting means being actuated in response to a signal applied thereto from an emitting control circuit;

(b) means for receiving an infrared beam reflected at said predetermined portion, asid infrared-receiving means producing an electrical signal coresponding to an intensity of an infrared beam reaching said infrared-receiving means after a reflection;

(c) means for detecting a fog on said windshield by comparing said electrical signal from said infrared-receiving means with a predetermined reference value and issuing a command signal indicative of the removal of the fog to actuate a fog removing apparatus provided in said vehicle in response to the direction of the fog;

(d) a timer circuit responsive to said command signal issuing means for causing said fog removing apparatus to continuously operate for a predetermined period of time after the absence of said command signal;

(e) first decision means for deciding that the fluctuation of said electrical signal is stably kept within a first predetermined range, after the removal of the fog performed in response to said command signal;

(f) second decision means for deciding that the deviation between said electrical signal and said predetermined reference value remains within a second predetermined range, after the decision of stability of the fluctuation; and (g) means for updating said predetermined reference value with a value of said electrical signal at the time that a decision is made by said second decision means.

5. A fog detecting apparatus for use in a vehicle, comprising:

(a) a plurality of infrared-emitters for emitting infrared beams such that the emitted infrared beams are respectively directed to a plurality of predetermined portions of a windshield of said vehicle, each of said infrared-emitter being actuated in response to a signal applied thereto from an emitting control circuit;

(b) a plurality of infrared receivers for receiving infrared beams reflected at said predetermined portions, each of said infrared-receivers producing an electrical signal corresponding to an intensity of an infrared beam reaching said infrared-receivers after a reflection;

(c) a plurality of detectors, each for detecting a fog on said windshield by comparing each of said electrical signals from each of said infrared-receivers with a predetermined reference value and issuing an command signal indicative of the presence of the fog in response to the detection of the fog;

(d) an OR circuit coupled to each of said detectors for generating a signal for actuating a fog removing apparatus provided in said vehicle in response to at least one command signal from said plurality of detectors;

(e) first decision means for deciding that the fluctuation of each of said electrical signals is stably kept within a first predetermined range, after the removal of the fog performed in response to said signal from said OR circuit;

(f) second decision means for deciding that the deviation between each of said electrical signals and said predetermined reference value remains within a second predetermined range, after the decision of stability of the fluctuation; and (g) means for updating said predetermined reference value with a value of one of said electrical signals at the time that a decision is made by said second decision means.

* * * * *